US011382502B2

(12) United States Patent
Bleicher et al.

(10) Patent No.: US 11,382,502 B2
(45) Date of Patent: Jul. 12, 2022

(54) SYSTEMS AND METHODS FOR PROVIDING SURFACE CONTRAST TO DISPLAY IMAGES FOR MICRO-SURGICAL APPLICATIONS

(71) Applicant: Duke University, Durham, NC (US)

(72) Inventors: Isaac Bleicher, Durham, NC (US); Moseph Jackson-Atogi, Durham, NC (US); Christian B. Viehland, Durham, NC (US); Cynthia Toth, Durham, NC (US); Joseph Izatt, Durham, NC (US)

(73) Assignee: Duke University, Durham, NC (US)

( * ) Notice: Subject to any disclaimer, the term of this patent is extended or adjusted under 35 U.S.C. 154(b) by 248 days.

(21) Appl. No.: 16/759,721

(22) PCT Filed: Nov. 30, 2018

(86) PCT No.: PCT/US2018/063308
§ 371 (c)(1),
(2) Date: Apr. 27, 2020

(87) PCT Pub. No.: WO2019/108934
PCT Pub. Date: Jun. 6, 2019

(65) Prior Publication Data
US 2021/0369104 A1 Dec. 2, 2021

Related U.S. Application Data

(60) Provisional application No. 62/592,794, filed on Nov. 30, 2017.

(51) Int. Cl.
*G06K 9/00* (2022.01)
*G01B 9/02* (2022.01)
(Continued)

(52) U.S. Cl.
CPC ............ *A61B 3/102* (2013.01); *A61B 3/0041* (2013.01); *A61B 3/1173* (2013.01);
(Continued)

(58) Field of Classification Search
USPC ........ 382/100, 103, 106–107, 117, 128, 132, 382/133, 154, 162, 168, 173, 181, 199,
(Continued)

(56) References Cited

U.S. PATENT DOCUMENTS

2007/0103693 A1* 5/2007 Everett .................. G06T 19/00
600/407
2009/0257636 A1* 10/2009 Wei ...................... A61B 3/0025
382/294

(Continued)

OTHER PUBLICATIONS

PCT Search Report and Written Opinion for PCT International Patent Application No. PCT/US18/63308, dated Apr. 25, 2019.
(Continued)

*Primary Examiner* — Seyed H Azarian
(74) *Attorney, Agent, or Firm* — Olive Law Group, PLLC

(57) ABSTRACT

Systems and methods for providing surface contrast to display images for micro-surgical applications are disclosed. According to an aspect, an imaging system includes an OCT apparatus configured to capture OCT data of an eye. The OCT image data can include depth-resolved images of reflected light intensity over a period of time. The imaging system also includes a controller configured to determine movement of the eye relative to the OCT imaging field-of-view. The controller may also determine a location within the imaged portion of the eye which tracks with the eye movement. Further, the controller may apply a color gradient to render OCT images of the eye based on a position relative to the determined location of the eye tracking location. The controller may also control a display to display the OCT images with the applied color gradient.

32 Claims, 6 Drawing Sheets

(51) Int. Cl.

| | |
|---|---|
| *A61B 3/10* | (2006.01) |
| *G06T 7/70* | (2017.01) |
| *G16H 30/20* | (2018.01) |
| *G16H 30/40* | (2018.01) |
| *A61B 3/00* | (2006.01) |
| *A61B 3/117* | (2006.01) |
| *A61B 3/12* | (2006.01) |
| *G06T 1/20* | (2006.01) |
| *G06T 7/00* | (2017.01) |
| *G06T 7/20* | (2017.01) |
| *G06T 11/00* | (2006.01) |
| *G16H 40/67* | (2018.01) |

(52) U.S. Cl.
 CPC .............. *A61B 3/1225* (2013.01); *G06T 1/20* (2013.01); *G06T 7/0012* (2013.01); *G06T 7/20* (2013.01); *G06T 7/70* (2017.01); *G06T 11/001* (2013.01); *G06T 11/008* (2013.01); *G16H 30/20* (2018.01); *G16H 30/40* (2018.01); *G06T 2207/10101* (2013.01); *G06T 2207/30041* (2013.01); *G16H 40/67* (2018.01)

(58) Field of Classification Search
 USPC ....... 382/214, 219, 254, 274, 285–291, 321, 382/294; 351/206; 345/589; 600/407, 600/356; 356/479
 See application file for complete search history.

(56) References Cited

U.S. PATENT DOCUMENTS

| | | | |
|---|---|---|---|
| 2012/0075584 A1* | 3/2012 | Stetson .................. | A61B 3/102 345/589 |
| 2013/0271757 A1* | 10/2013 | Kang ..................... | A61B 3/102 356/479 |
| 2016/0089020 A1* | 3/2016 | Gomi ................... | A61B 3/0041 351/206 |
| 2021/0075584 A1* | 3/2021 | Babich .................. | H04H 20/26 |

OTHER PUBLICATIONS

Knecht, P. et al. "Use of Introperative Fourier-Domain AnteriorSegment Optical Coherence Tomography During Descemet Stripping Endothelial Keratoplasty," American Journal of Ophthalmology, Sep. 2010, 360-365.e2, 150 (3), Elsevier, Amsterdam, Netherlands.

Ehlers, J. et al. "Utility of Intraoperative Optical Coherence Tomography During Vitrectomy Surgery for Vitreomacuair Traction Syndrome," Retina, Jul. 2014, 34(7), 1341-1346, National Institute of Health (NIH), Betheseda, United States.

Ehlers, J. et al. "Novel Microarchitectural Dynamics in Rhegmatogenous Retinal Detachments Identified With Intraoperative Optical Coherence Tomography," The Journal of Retinal and Vitreous Diseases, 2013, 33(7), 1428-1434, BioMed Central, Ltd. (Springer Nature), London.

Ehlers, J. et al. "Analysis of Pars Plana Vitrectomy for Optic Pit-Related Maculopathy With Intraoperative Optical Coherence Tomography," Arch Ophthalmol, 2011, 129(11), 1483-1486, American Medical Association (AMA), Chicago, IL, United States.

Carrasco-Zevallos, O. et al. "4D microscope-integrated OCT improves accuracy of ophthalmic surgical maneuvers," Proc. SPIE, Mar. 4, 2016, 9693, 969306-1-969306-7, SPIE, Bellingham, Washington, United States.

Heiland, M. et al. "Intraoperative imaging of zygomaticomaxillary complex fractures using a 3D C-arm system," International Journal of Oral and Maxillofacial Surgery, 2005, 34, 369-375, Elsevier, Amsterdam, Netherlands.

Senft, C. et al. "Intraoperative MRI guidance and extent of resection in glioma surgery: a randomised, controlled trial," Lancet Oncology, 2011, 12, 997-1003, Elsevier, Amsterdam, Netherlands.

Tormenti, M. et al. "Intraoperative computed tomography image-guided navigation for posterior thoracolumbar spinal instrumentation in spinal deformity surgery," Neurosurg Focus, Mar. 2010, 28(3), 1-6, American Association of Neurological Surgeons (AANS), Rolling Meadows, Illinois.

Zausinger, S. et al. "Intraoperative Computed Tomography Wth Integrated Navigation System in Spinal Stabilizations," SPINE, 2009, 34(26), 2919-2926, Lippincott Williams & Wilkins, Philadelphia, PA.

Roth, J. et al. "Real-Time Neuronavigation with High-Quality 3D Ultrasound SonoWand in Pediatric Neurosurgery," Pediatric Neurosurgery, 2007, 43, 185-191, Karger, Basel, Switzerland.

Carrasco-Zevallos, O. et al. "Review of intraoperative optical coherence tomography: technology and applications [Invited]," Biomedical Optics Express, Mar. 1, 2017, 8(3), 1607-1637, OSA Publishing (Optical Society of America (OSA)), Washington, D.C.

Tao, Y. et al. "Microscope-integrated intraoperative OCT with electrically tunable focus and heads-up display for imaging of ophthalmic surgical maneuvers," Biomedical Optics Express, Jun. 1, 2014, 5(6), 1877-1885, OSA Publishing, Washington, D.C.

Zhang, K. et al. "Real-time intraoperative 4D full-range FD-OCT based on the dual graphics processing units architecture for microsurgery guidance," Biomedical Optics Express, Apr. 1, 2011, 2(4), 764- 770, OSA Publishing, Washington, D.C., United States.

Shen, L. et al. "Novel microscope-integrated stereoscopic heads-up display for intrasurgical optical coherence tomography," Biomedical Optics Express, May 1, 2016, 7(5), 1711-1726, OSA Publishing, Washington, D.C., United States.

Viehlad, C. et al. "Enhanced volumetric visualization for real time 4D intraoperative ophthalmic swept-source OCT," Biomedical Optics Express, May 1, 2016, 7(5), 1815-1829, OSA Publishing, Washington, D.C., United States.

Carrasco-Zevallos, O. et al. "Live volumetric (4D) visualization and guidance of in vivo human ophthalmic surgery with intraoperative optical coherence tomography," Scientific Reports, Aug. 19, 2016, 6 (31689), 1-16, Nature Research (Springer Nature), London.

Ehlers, J. et al. "The Prospective Intraoperative and Perioperative Ophthalmic ImagiNg with Optical CoherEncE TomogRaphy (PIONEER) Study: 2-year Results," Am J Opthalmol, Nov. 2014, 158(5), 999-1007, NIH, Betheseda, United States.

Ahlers, C. et al. "Automatic segmentation in three-dimensional analysis of fibrovascular pigmentepithelial detachment using high-definition optical coherence tomography," Br J Ophthalmol, Oct. 26, 2007, 92, 197-203, BMJ, London, United Kingdom.

Loduca, A. et al. "Thickness Mapping of Retinal Layers by Spectral Domain Optical Coherence Tomography," Am J Ophthalmol, Dec. 2010, 150(6), 849-855, Elsevier, Amsterdam, Netherlands.

Beenakker, J. et al. "Automated Retinal Topographic Maps Measured With Magnetic Resonance Imaging," Investigative Ophthalmology & Visual Science, Feb. 2015, 56(2), 1033-1039, The Association for Research in Vision and Ophthalmology, Inc, Rockville, MD, United States.

Oh, I. et al. "Retinal Topography of Myopic Eyes: A Spectral-Domain Optical Coherence Tomography Study," Investigative Ophthalmology & Visual Science, Jul. 2014, 55(7), 4313-4319, The Association for Research in Vision and Ophthalmology, Inc, Rockville, MD, United States.

Nimsky, C. et al. "Quantification of, Visualization of, and Compensation for Brain Shift Using Intraoperative Magnetic Resonance Imaging," Neurosurgery, Nov. 2000, 47(5), 1070-1080, Congress of Neurological Surgeons (Oxford University Press), United Kingdom.

Chandra, S. et al. "Characterization of Degenerative Mitral Valve Disease Using Morphologic Analysis of Real-Time Three-Dimensional Echocardiographic Images," Ciro Cardiovasc Imaging, Jan. 2011, 24-32, American Heart Association, Dallas, TX, United States.

Tsang, W. et al. "The Value of Three-Dimensional Echocardiography Derived Mitral Valve Parametric Maps and the Role of Experience in the Diagnosis of Pathology," Journal of the American Society of Echocardiography, Aug. 2011, 24(8), 860-867, The American Society of Echocardiography, Durham, NC.

(56) References Cited

OTHER PUBLICATIONS

Smith, M. et al. "Methods for the visualization of digital elevation models for landform mapping," Earth Surface Processes and Landforms, 2005, 30, 885-900, John Wiley & Sons Ltd, Hoboken, NJ, United States.
Carrasco-Zevallos, O. et al. "Constant linear velocity spiral scanning for near video rate 4D OCT ophthalmic and surgical imaging with isotropic transverse sampling," Biomedical Optics Express, Oct. 1, 2018, 9(10), 5052-5070, OSA, Washington, D.C., United States.
Parischa, N. et al. "Real-Time Microscope-Integrated OCT to Improve Visualization in DSAEK for Advanced Bullous Keratopathy" Cornea, Dec. 2015, 34(12), 1606-1610, HHS, Washington, D.C., United States.
Parischa, N. et al. "4D Microscope-Integrated OCT to Visualize Suture Depth in Strabismus Surgery," J Pediatr Ophthalmol Stabismus, May 22, 2018, 54, e1-e5, HHS, Washington, D.C., United States.
Kumar, A. et al. "Utility of microscope-integrated optical coherence tomography (MIOCT) in the treatment of myopic macular hole retina! detachment," BMJ Case Rep, Jun. 15, 2017, 1-4, BMJ, London, United Kingdom.
International Search Report and Written Opinion in related app. PCT/US18/63308 dated Apr. 25, 2019 (11 pages).
International Preliminary Report in related app. PCT/US2018/063308 dated Jun. 2, 2020 (6 pages).

\* cited by examiner

SYSTEMS AND METHODS FOR PROVIDING SURFACE CONTRAST TO DISPLAY IMAGES FOR MICRO-SURGICAL APPLICATIONS

CROSS REFERENCE TO RELATED APPLICATION

This application is a 371 application of PCT International Patent Application No. PCT/US2018/063308, filed on Nov. 30, 2018, and titled SYSTEMS AND METHODS FOR PROVIDING SURFACE CONTRAST TO DISPLAY IMAGES FOR MICRO-SURGICAL APPLICATIONS, which claims priority to U.S. Patent Application No. 62/592,794, filed Nov. 30, 2017, and titled SYSTEMS AND METHODS FOR PROVIDING SURFACE CONTRAST IN RENDERING OF THREE-DIMENSIONAL IMAGES FOR MICRO-SURGICAL APPLICATIONS; the contents of which are incorporated herein by reference in their entireties.

FEDERALLY SPONSORED RESEARCH OR DEVELOPMENT

This invention was made with government support under grant number R01-EY023039 awarded by the National Institutes of Health/National Eye Institute Biomedical Research Partnership, and grant number P30-EY005722 awarded by the National Eye Institute (NEI). The government has certain rights to this invention.

TECHNICAL FIELD

The presently disclosed subject matter relates generally to medical devices. Particularly, the presently disclosed subject matter relates to systems and methods for providing surface contrast to display images for micro-surgical applications.

BACKGROUND

Advances in imaging and computer processing speeds have enabled development of improved intraoperative imaging techniques. Volumetric rendering of data collected peri- and intra-operatively has been adopted to guide surgical planning and maneuvers in ophthalmology, neurosurgery, orthopedic surgery, and reconstructive surgery. Volumetric display creates a view of the surgical field that can be intuitively manipulated and interacted with to provide critical feedback to both trainee and experienced surgeons.

In ophthalmology, microscope-integrated optical coherence tomography (MIOCT) is being increasingly used to augment the en face-only view of the operating microscope in both posterior and anterior segment settings. Live, three-dimensional (3D) rendering of OCT scans and visualization on a heads-up display have been developed. These technologies allow for intraoperative imaging and real-time guidance of surgical maneuvers and have been shown to improve visualization of epiretinal membrane elevation, localization of instruments, and monitoring of retinal contour deformation during surgery. As surgeon experience with these systems has developed, it has started to impact surgical decision-making.

MIOCT faces a fundamental data visualization issue as the scanning technology advances. The issue is whether the surgeon view and analyze large quantities of continuously changing OCT data while actively operating and remaining safe in surgery. Current volumetric renders have been insufficient in solving this problem. As a three-dimensional (3D) object is compressed into a two-dimensional (2D) display, foreground, midground, and background structures can be difficult to resolve, and instruments may be difficult to differentiate from surrounding tissue. Artificial shadowing, stereoptic displays, and rotation of the rendered volume can be used to highlight boundaries between surfaces but they remain insufficient solutions, adding complexity to the MIOCT system and its operation. These issues have limited MIOCT volumes to ancillary intraoperative use and reinforced the need for the traditional optical view through the microscope.

In other settings, colorization of medical imaging has been used to provide contextual information for complex 3D structures to address this data visualization question. Topographical maps have been used to visualize table-top OCT and MRI scans of the retina in evaluation of myopia, retinal detachment and AMD. In other fields, position-based colorization of 3D ultrasound scans of the mitral valve assists cardiac surgeons intraoperatively, and colorized mapping of brain shift guides neurosurgical tumor resection. Additionally, non-medical fields such as earth and atmospheric science widely use colorization for topography of 3D mappings. The addition of data overlain on the 3D volume improves interpretation of complex imaging.

However, colorization of volumetric imaging has not been applied to data acquired in real time to guide surgical maneuvers due to computational challenges. To be useful, colorization should carry meaning not otherwise inherent in the volume. This requires additional computation time which can add to lag between image capture and display to the surgeon. Second, real-time imaging of surgical fields is subject to motion induced by the patient, surgeon, and/or instrumentation. In view of the foregoing, there is a need for improved medical devices and techniques for overcoming these difficulties to improve imaging, particularly OCT imaging.

BRIEF DESCRIPTION OF THE DRAWINGS

Figure 1:
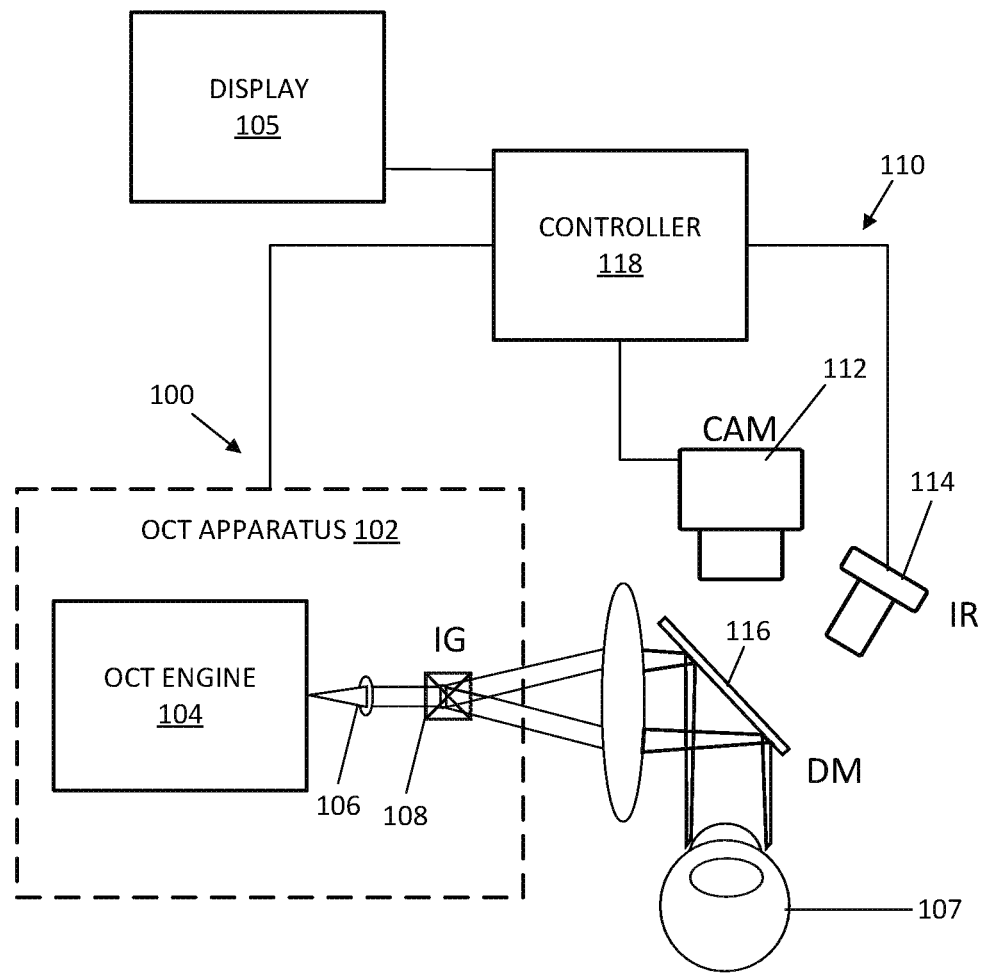
Figure 2:
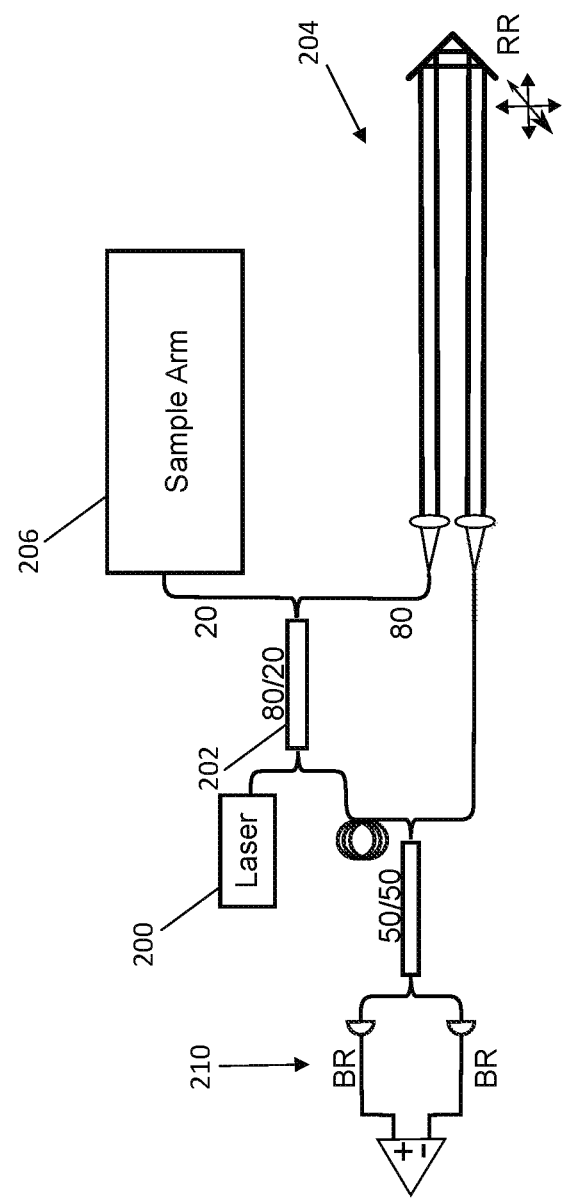
Figures 5A, 5B, 5C, 5D:
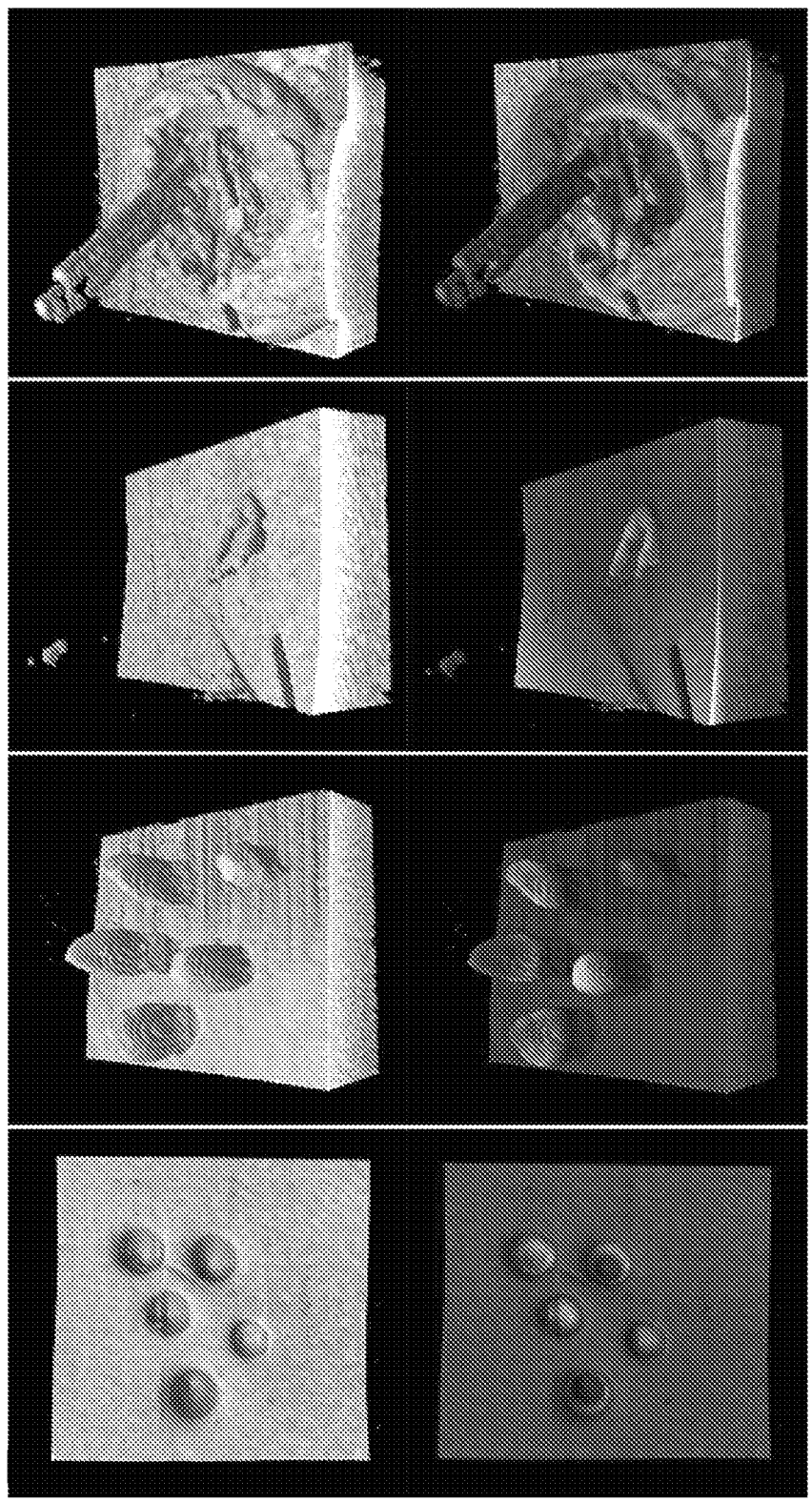
Figure 6:
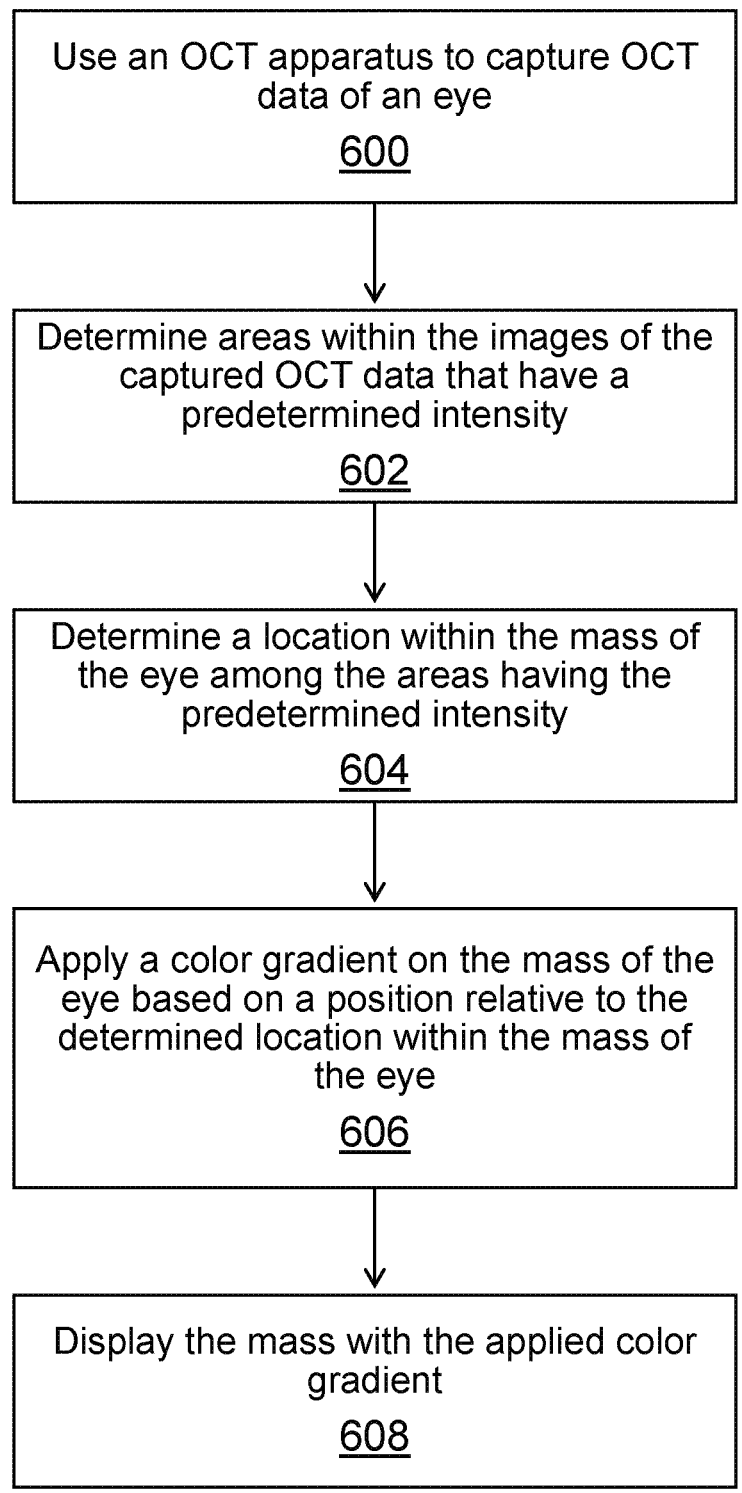

Having thus described the presently disclosed subject matter in general terms, reference will now be made to the accompanying Drawings, which are not necessarily drawn to scale, and wherein:

FIG. 1 is a schematic diagram of an example imaging system in accordance with embodiments of the present disclosure;

FIG. 2 is a schematic diagram of an example OCT engine in accordance with embodiments of the present disclosure;

FIGS. 3A-3D are images of MIOCT volumes and B-scans that demonstrate the colorization and stabilization process in accordance with embodiments of the present disclosure;

FIGS. 4A-4D are images of grayscale and colorized (grayscale in the images) MIOCT volumes from membrane peeling cases shown during intraoperative volume testing;

FIGS. 5A-5D are images of grayscale and colorized MIOCT volume samples from each microsurgical skill; and FIG. 6 is a flow diagram of an example method of imaging an eye in accordance with embodiments of the present disclosure.

SUMMARY

The presently disclosed subject matter provides systems and methods for providing surface contrast to display images for micro-surgical applications. According to an aspect, an imaging system includes an OCT apparatus configured to capture OCT data of an eye. The OCT image data can include depth-resolved images of reflected light intensity over a period of time. The imaging system also includes a controller configured to determine movement of the eye relative to the OCT imaging field-of-view. The controller may also determine a location within the imaged portion of the eye which tracks with the eye movement. Further, the controller may apply a color gradient to render OCT images of the eye based on a position relative to the determined location of the eye tracking location. The controller may also control a display to display the OCT images with the applied color gradient.

According to another aspect, an imaging system includes an OCT apparatus configured to capture OCT images of an object. The imaging system also includes a controller configured to apply a color gradient to rendered OCT images of the object based on depth within the image. Further, the controller is configured to control a display to display OCT images with the applied color gradient.

DETAILED DESCRIPTION

The following detailed description is made with reference to the figures. Exemplary embodiments are described to illustrate the disclosure, not to limit its scope, which is defined by the claims. Those of ordinary skill in the art will recognize a number of equivalent variations in the description that follows.

Articles "a" and "an" are used herein to refer to one or to more than one (i.e. at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result.

The use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of and "consisting of those certain elements.

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

In accordance with embodiments of the present disclosure, systems and methods are provided for applying colorization to MIOCT volumes based on depth, and for stabilizing the color gradient relative to the scanned object's axial motion. These systems and methods are provided because: 1) colorization can improve perspective of thickness and relative positioning in 3D volumes as compared with grayscale volumes; 2) use of colorization intraoperatively can allow for faster and more accurate microsurgical maneuvers; 3) stabilization against a relative reference point can increase colorization utility in real-life surgical scenarios when axial motion is significant; 4) and with improved visualization with colorization, microsurgical maneuvers may be performed without the microscope optical view. In accordance with embodiments of the present disclosure, speed optimized algorithms or methods are provided for assigning color for imaging in real time or near-real time.

FIG. 1 illustrates a schematic diagram of an example imaging system 100 in accordance with embodiments of the present disclosure. This system may be used for imaging of the anterior segment of an eye. Referring to FIG. 1, the imaging system 100 may include an OCT apparatus 102 configured to generate OCT images of an eye 107. A display 105 may display the generated OCT images. Example displays include, but are not limited to, a heads-up display (HUD) within the microscope oculars of an OCT system, a conventional computer monitor, an external 3D television display, or the like. The OCT apparatus 102 may include an OCT engine 104, a lens 106, and an imaging galvanometer 108. Any suitable OCT engine may be utilized as will be understood by those of skill in the art.

FIG. 2 illustrates a schematic diagram of an example OCT engine 104 in accordance with embodiments of the present disclosure. The OCT engine 104 in this example is a swept-source OCT (SSOCT) engine, although it should be understood that any suitable type of OCT engine may be utilized. This example OCT engine 104 may be used together with any of the other examples disclose herein, such as in place of the OCT engine 104 shown in FIG. 2, more detail of which follows. A scanner may introduce the OCT light into the infinity space of the surgical microscope such that the OCT and microscope views are parfocal and coaxial.

Referring to FIG. 2, the OCT engine 104 may include a laser 200. As an example, the laser 200 may be a swept-frequency laser centered at 1040 nm, with a tuning bandwidth of 100 nm and a repetition rate of 100 kHz for illuminating a Mach-Zehnder interferometer 202. Light returning from the reference arm 204 and sample arm 206 may be collected with a balanced receiver 210 (such as a receiver manufactured by Thorlabs, Inc., of Newton, N.J.). A digitizer (such as a digitizer manufactured by AlazarTech, Inc., of Pointe-Claire, QC, Canada) may digitize the interferometric signal and the k-clock from the swept source. The OCT system may be controlled by suitably-configured software. In experimentation in a retinal imaging configuration, the system achieved a depth range of 3.7 mm and a peak sensitivity of 101 dB.

The imaging system 100 may include an eye tracking device 110 configured to determined movement of an eye. For example now turning to FIG. 1, the imaging system 100 includes a camera 112 positioned and configured to capture a sequence of images or video of the eye 107. Video of the pupil of the eye 107 may be obtained, for example, using a high-speed camera (e.g., Edmund Optics USB 3.0 Machine Vision Camera, Edmund Optics; Barrington, N.J.) with a maximum frame rate of 100 frames per second (FPS). The eye tracking device 110 may also include a light source 114 such as, but not limited to, a light emitting diode (LED). In an example, the eye 107 may be illuminated with an 850 nm LED (e.g., an LED available from Thorlabs, of Newton, N.J.). To co-align the infrared (IR) illumination with the optical axis of the OCT system, the camera 112 and light source 114 may be placed behind a short-pass dichroic mirror 116 with a cutoff at 960 nm. The IR illumination may be transmitted through the pupil. In addition, the IR illumination may be reflected by the iris, sclera, and the surrounding skin yielding images with a bi-modal histogram that allowed for segmentation.

The imaging system 100 may include a controller 118 for processing images captured by the eye tracking device 110. For example, the controller 118 may include suitable hardware, software, firmware, or combinations thereof for implementing the functionality described herein. The functions may be implemented by one or more processors and memory, for example.

In accordance with embodiments, color mapping may be integrated into the MIOCT rendering process. The controller 118 shown in FIG. 1 may implement color mapping. In an example, a unique color may be assigned to several positions along the B-scan axial dimension and a color gradient applied as a linear interpolation in the RGB color space between each position. Axial positions above the most superficial position and below the deepest position are assigned, by the controller 118, the color of those respective positions. When rendering the volume, voxels at particular depths are assigned a color as specified by the gradient.

The controller 118 may assign color gradients relative to the volume reflectivity's center of mass in the axial direction, or some other appropriate measure of gross volume axial displacement, to stabilize colors relative to movement of the scanned object. Before each volume is rendered, a histogram of pixel intensity values is constructed for the fully processed OCT data and a threshold value at the $99^{th}$ percentile of pixel intensity identified. All voxels with reflectivity below this threshold may be eliminated, isolating the brightest surface that can be tracked between volumes. When imaging the retina, this surface is typically the retinal pigmented epithelium. The axial center of mass of this data may be calculated using the formula:

$$\text{Center of } Mass_k = \frac{\sum_i \sum_j \sum_k k * A(i, j, k)}{\sum_i \sum_j \sum_k A(i, j, k)}.$$

Figures 3A, 3B, 3C, 3D:
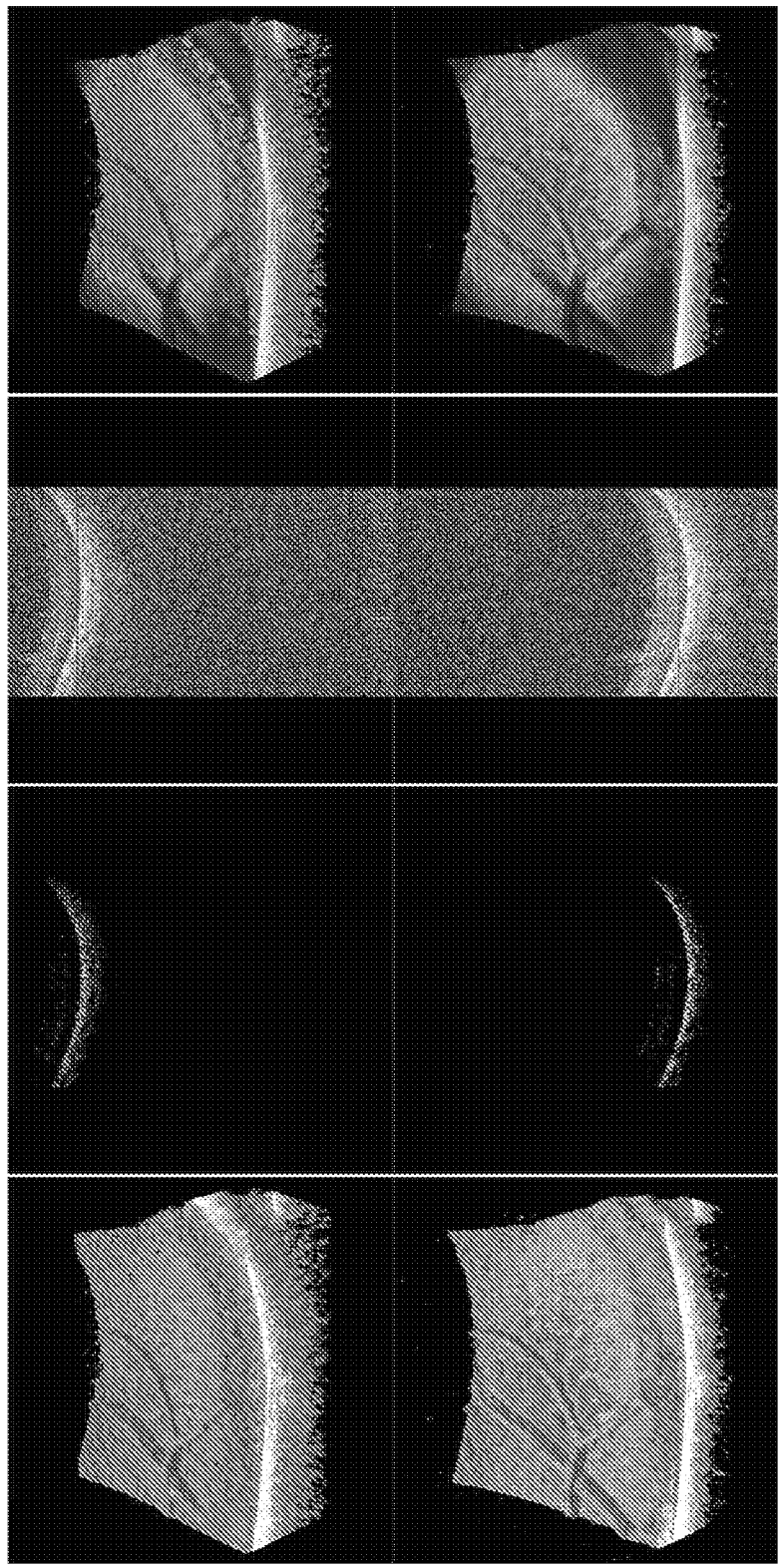

Here i, j, k represent the fast-scanning, slow-scanning and axial dimensions of the MIOCT volume data respectively and A(i, j, k) represents the voxel intensity at a specific location in the scan. The color gradient may subsequently be specified based on positions relative to this center of mass. As a result, color changes due to movements of the scanned surface (i.e., from patient motion, surgical manipulation, etc.) are mitigated. For example, FIGS. 3A-3C are images of MIOCT volumes and B-scans that demonstrate the colorization and stabilization process in accordance with embodiments of the present disclosure. In particular, FIG. 3A is an image showing a non-colorized MIOCT volume filtered with a threshold at the $99^{th}$ percentile of reflectivity values. FIG. 3B is an image showing a non-colorized MIOCT volume in which center of mass is calculated. FIG. 3C is an image showing application of color (shown in grayscale in this figure). FIG. 3D is an image showing top and bottom sequences that demonstrate stability with axial motion. It is noted that in these examples depicting grayscale of color images, volumes are colorized in the actual images such that the highest features red, the lowest features are blue and intermediate features are yellow. Features at heights between these layers are colored according to a linear gradient along the RGB colorspace.

In accordance with embodiments, a large quantity of data may be processed in real-time by use of an algorithm written utilizing a parallel computational approach (by use of the NVIDIA CUDA Toolkit, available from NIVIDIA Corporation of California, U.S.A.) on a graphics processing unit (GPU). It is noted that this is but one example of processing; however, it is noted that any other suitable computing devices or equipment may be utilized. Performance analysis was conducted using a GPU profiler (by use of the NVIDIA Visual Profiler, available from NIVIDIA Corporation of California, U.S.A.) to measure the time to calculate center of mass and apply colorization.

OCT volume depth colorization and its axial stabilization using the axial center of mass approach were validated using two models: layered tape (3M, Minnesota, USA) to emulate retinal layers and a porcine eye. This study adhered to the ARVO Animal Statement principles in the use of porcine eyes. The model was translated across the scanning range of the MIOCT system in discrete increments of 1 mm and the calculated center of mass recorded at each position. Validation was achieved by comparison of changes in the calculated center of mass against the known movement of the stage. Expert review of the MIOCT volumes was performed to assess subjective stability of the colorization. The speed optimized algorithms or methods are provided for assigning color to these volumes for imaging in real time or near-real time.

Depth colorization was applied to pre-recorded 4D MIOCT data from previous human vitreoretinal surgeries. Experienced surgeons (N=7) were shown a combination of five grayscale still volumes and videos of surgical membrane peeling (Supplementary Document S1) and asked to determine for each whether retinal membranes were differentiable from retina, whether an instrument was present in the volume, whether the instrument was in contact with tissue and/or deforming the retina if present. Surgeons were then shown each volume using depth colorization and asked to reassess using the same questions. Their subjective preference for color or grayscale was also recorded for each volume. Survey responses were compared with independent review of B-scans from the volumetric data as the gold standard. Statistical testing was performed using McNemar's test for paired, nominal data with a significance level of 0.05.

The MIOCT scanner described herein was used to display volumes in stereo on an external, 65-inch, 3D OLED television, viewed with polarized glasses. B-scans of the volumes were available to the MIOCT operator and retrospectively to the grader but not to the participants. The optical view through the microscope was obscured to ensure that the participants were using the OCT only. Two sets of scanning parameters were used: a 10 mm×10 mm×3.7 mm field of view with 350×96×800 voxels for the thickness identification task and a 5 mm×5 mm×3.7 mm field of view with 250×85×800 for the other tasks to provide smoother surgical guidance. Colorization was applied with red superiorly, yellow medially, and blue inferiorly and the color boundaries set across 20% of the volume at positions described for each skill below.

Scenes each containing five objects of varying height either elevated from a flat surface or recessed into a flat surface were constructed from clay (Polyform Products Company, Illinois, USA). Color gradients were positioned across the range of object heights and/or depths. Subjects were shown each scene sequentially as an MIOCT volume and were asked to rank each of the five objects by thickness on a provided scoring sheet. They were not permitted to directly see or manipulate the object during testing. The time to complete each assessment and the number of incorrect assessments were recorded for each object. This test was repeated 5 times with elevated objects and five times with recessed objects.

A globe eye model was composed of a posterior, flat, clay, 2 cm diameter surface with an elevated rim covered by a soft plastic hemisphere (Phillips Studio, Bristol, UK) with apex cut away to allow for MIOCT visualization of the clay and a 25 g cannula (Alcon, Tex., USA) 3 mm posterior to the cut-away margin of the hemisphere.

Subjects were provided with a flexible loop and instructed to bring the tip of the loop as close to the surface as possible without touching. Each trial was stopped when the subject indicated that they were satisfied with the position of the instrument. Color gradients were positioned such that the surface was blue and yellow indicated the space immediately above the surface. The time to complete this task was recorded. MIOCT data was recorded and retrospective analysis identified the closest position of the instrument to the surface in the volumes 2-3 volumes from the final volume. These volumes were used to minimize the impact of inadvertent motion of the instrument as the subject indicated completion. The distance between the instrument and the surface was measured and recorded. This trial was repeated 4 times.

The model eye described above was used in this task. A 4 mm diameter clay ring was placed on the clay surface and a 2 mm square of transparency film was folded to form a V-shape and placed within the clay ring. Subjects were instructed to use a 25 g forceps to remove the object without contacting surrounding structures. Color gradients were positioned such that the surface was blue and the ring and object were yellow and red. The time to complete this task was recorded. MIOCT data was recorded and retrospective analysis recorded the number of grasps (closure of the forceps) and inadvertent contacts with the underlying surface. This trial was repeated 3 times.

Figures 4A, 4B, 4C, 4D:
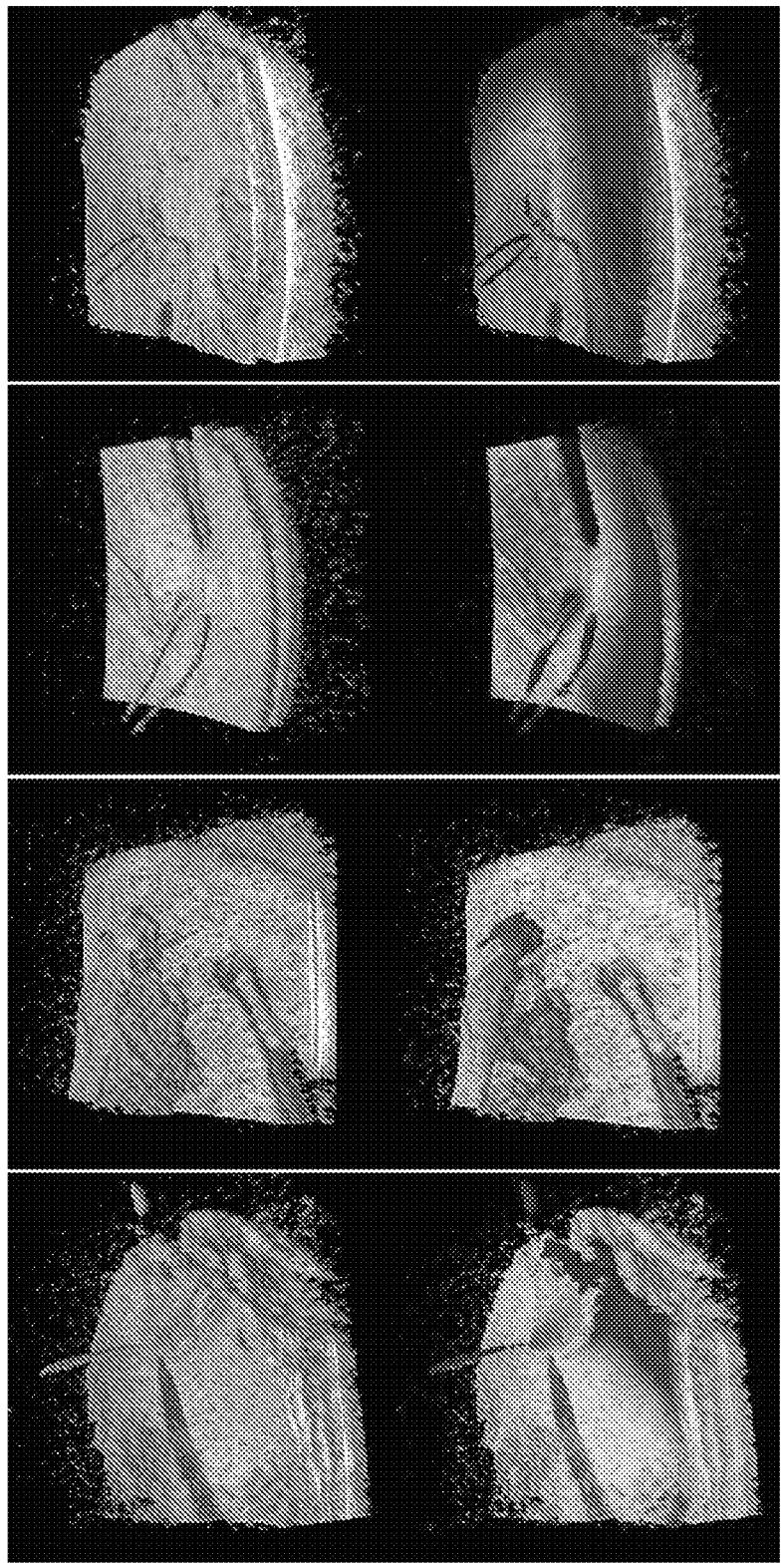

FIGS. 4A-4D are images of grayscale and colorized (grayscale in the images) MIOCT volumes from membrane peeling cases shown during intraoperative volume testing. Particularly, FIG. 4A shows membrane being pulled by forceps. FIG. 4B shows retina deformation by flexible loop. FIG. 4C shows the flexible loop above the retina surface. FIG. 4D shows a grayscaled color image. Color was applied with red superiorly, yellow medially, and green inferiorly. Color boundaries were individually chosen to highlight surface features. It is noted that in these examples depicting grayscale of color images, volumes are colorized in the actual images such that the highest features are red, the lowest features are blue and intermediate features are yellow. Features at heights between these layers are colored according to a linear gradient along the RGB colorspace.

FIGS. 5A-5D are images of grayscale (top) and colorized (bottom, grayscale in the images) MIOCT volume samples from each microsurgical skill. FIGS. 5A and 5B show example surfaces with recessed and elevated objects, respectively. FIG. 5C show the object grasp skill with the forceps attempting to grasp a membrane-like object. FIG. 5D shows color applied with red superiorly, yellow medially, and blue inferiorly. Color boundaries were applied just above the surface. While these figures use 2D representations of the 3D volume, subjects viewed stereoptic images while completing each task. It is noted that in these examples depicting grayscale of color images, volumes are colorized in the actual images such that the highest features red, the lowest features are blue and intermediate features are yellow. Features at heights between these layers are colored according to a linear gradient along the RGB colorspace.

In accordance with embodiments of the present disclosure, systems and methods are disclosed that provide contrast between various elements of the surgical field by applying a color gradient to the 3D volume produced by the MIOCT system. The present disclosure provides, in part, systems and methods for providing contrast between various elements of the surgical field by applying a color gradient to the three-dimensional volume produced by the MIOCT system. In the systems and methods provided herein, the color gradient signals the position of imaging voxels along the axial dimension. Not only does this allow for identification of an object's position along the axial dimension but also provides 3D perspective of and differentiation between uneven or layered surfaces, surgical instrumentation and other objects of interest across the scanning volume. This feedback allows surgeons to orient themselves to areas of interest, perform microsurgical maneuvers under careful observation of surgical instrumentation and monitor inadvertent distortion of the surrounding field. In some embodiments, the applied color is used to signal any other measured property of the object as described below.

In some embodiments, the color gradient may be applied as a post-processing effect on the OCT data in the scanning software as the data is acquired and displayed or during post-procedure data analysis. A number of user-specified positions along the B-scan axial dimension determines the fixed color positions. Users may use a suitable user interface to specify a unique color for each of these positions. In another embodiment, between each pair of positions along the axial dimension, a linear color gradient can be applied. In yet other embodiments, axial positions above or below the two extremity values may be assigned the color of the closest user-specified color without a gradient. For all acquired volumes, voxels lying at a particular position along the axial dimension take on the color assigned as described above. The speed optimized algorithms or methods are provided for assigning color to such volumes for imaging in real time or near-real time.

In some embodiments, the color gradient as described above may remain fixed as surgical motion or changes in microscope focus alter the object of interest's position along the axial dimension of the OCT scan. As a result, the object of interest may not have a constant color gradient applied to it and the color changes with these motions.

In another embodiment, a surface within the scanned volume is identified and a fixed reference point on the scanned volume is provided. In some embodiments, this reference point can be a continuously updated position that serves as a basis for the color gradient. In other embodiments, processed OCT volumetric data can be filtered to remove the lowest percentiles of pixel intensity values. This effectively isolates the brightest layer (in the case of retinal surgery, the retinal pigmented epithelium) or other components and provides a stable reference for the scanned object position along the axial dimension. A pixel intensity weighted calculation along the axial dimension provides a single-dimensional center of mass for the volume. In some embodiments, this center of mass can be calculated in real time prior to the display of the OCT volume, allowing for continuous stabilization of the color gradient. The user defined color positions that establish the color gradient can then set relative to this position along the axial dimension. Color gradients can be applied to the OCT volume as described above.

This application of a stabilized color gradient relative to the center of mass of the object of interest solves a significant problem in intraoperative MIOCT applications. Imaging has previously been limited by surgical, patient, or equipment motion preventing the use of more sophisticated image processing and analysis. With this approach, we can reliably calculate a fixed reference position in near real time to provide a basis for further image processing. The novel approaches disclosed herein has been applied to stabilization of an axial-depth color gradient but could also be used to update the reference arm to provide tracking of the scanned image itself.

While the systems and methods provided herein for stabilization and color application is stable and effective, there are a number of other approaches to calculate a stable reference point. Accordingly, in one embodiment this is done with layer segmentation using an edge-finding algorithm, breaking the surface into sub-segments and calculating each area individually, or taking a center of mass over unfiltered data. Color gradients are applied equally across the entire volume or may be applied segmentally, for example to account for curved surfaces. While in some embodiments linear color gradients have been chosen to indicate axial position, color gradients can be non-linear, the indication of depth can be performed with grayscale, and visual or auditory warnings indicating position can be separated from the image display. The speed optimized algorithms or methods are provided for assigning color to these volumes for imaging in real time or near-real time.

Furthermore, color may be used to provide contrast within the volumes based on measures other than axial position. It may indicate particular layers within the object of interest, identify a window of safety for surgical maneuvers or identify any other measured property of the imaged volume. As an indication of position, systems and method are operate in the axial dimension but may be used along any other suitable dimension within the scanned volume.

Finally, while this technique was developed in a retinal surgery environment with OCT-generated volumes, this innovation would apply to any imaging-assisted medical procedure. Many medical environments require imaging and procedural manipulation of small tissues and have to manage movement of the field of interest. While the presently disclosed subject matter was demonstrated with OCT, it may be applied to any other imaging modality for center of volume or center of mass. The above described technique may be applied to image stabilization and improved 3D resolution of the working space in any of these applications.

In accordance with embodiments of the present disclosure, FIG. 6 illustrates a flow diagram of an example method of imaging an eye. The method of FIG. 6 is described as being implemented by the imaging system 100 shown in FIG. 1; however, it should be noted that the method may be implemented by any other suitable system as will be understood by those of skill in the art.

Referring to FIG. 6, the method includes using 600 an OCT apparatus to capture OCT data of an eye. For example, the OCT apparatus 102 shown in FIG. 1 may be used to capture OCT data of the eye 107. The OCT data, in this example, is 3D image data (e.g., voxels) of the eye captured by the OCT apparatus 102 over a period of time. The OCT data can include images of a mass of the eye over a period of time. For example, the OCT data may include image data of the retina of the eye.

The method of FIG. 6 includes determining areas 602 within the images of the mass of the eye that have a predetermined intensity. For example, the controller 118 shown in FIG. 1 may generate a histogram of pixel intensity values for the fully processed OCT data before rendering each volume. The controller 118 may subsequently determine areas within the images of the mass of the eye 107 having the predetermined intensity in the $99^{th}$ percentile of intensity. These areas may be voxels of images of the mass of the eye. This particular area of the eye may be the retinal pigmented epithelium. Voxels with a reflectivity below a predetermined threshold (e.g., $99^{th}$ percentile) may be eliminated to thereby isolate the brightest surface that can be tracked between volumes.

The method of FIG. 6 includes determining 604 a location within the mass of the eye among the areas having the predetermined intensity. For example, the controller 118 may determine a location that is the center or the approximate center of the mass or volume. The axial center of mass of this data may be calculated using a suitable technique such as the formula described herein.

The method of FIG. 6 includes applying 606 a color gradient on the mass of the eye based on a position relative to the determined location within the mass of the eye. For example, the controller 118 may specify the color gradient based on positions relative to the determined center of mass. As a result, color changes due to movements of the scanned surface (e.g., from patient motion, surgical manipulation, etc.).

It is noted that the controller 118 may include a GPU configured to implement the functions of steps 600, 602, 604, and 606 in a parallel computational technique. An example benefit of the use of parallel computation is that a large quantity of data can be processed in real-time.

The method of FIG. 6 includes displaying 608 the mass with the applied color gradient. For example, the controller 118 may control the display 105 for displaying the mass with the applied color gradient.

The example method of FIG. 6 can be integrated into a MIOCT rendering process. The method can assigned a unique color to several positions along the B-scan axial dimension and apply a color gradient as a linear interpolation in the RGB color space between each position. Axial positions above the most superficial position and below the deepest positions can be assigned the color of those respective positions. When rendering the volume, voxels at particular depths can take on color as specified by the gradient. This color representation may be displayed to the user.

The present subject matter may be a system, a method, and/or a computer program product. The computer program product may include a computer readable storage medium (or media) having computer readable program instructions thereon for causing a processor to carry out aspects of the present subject matter.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a RAM, a ROM, an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network, or Near Field Communication. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present subject matter may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++, Javascript or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present subject matter.

Aspects of the present subject matter are described herein with reference to flowchart illustrations and/or block diagrams of methods, apparatus (systems), and computer program products according to embodiments of the subject matter. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present subject matter. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the embodiments have been described in connection with the various embodiments of the various figures, it is to be understood that other similar embodiments may be used, or modifications and additions may be made to the described embodiment for performing the same function without deviating therefrom. Therefore, the disclosed embodiments should not be limited to any single embodiment, but rather should be construed in breadth and scope in accordance with the appended claims.

REFERENCES

1. Knecht P B, Kaufmann C, Menke M N, Watson S L, Bosch M M. Use of Intraoperative Fourier-Domain Anterior Segment Optical Coherence Tomography During Descemet Stripping Endothelial Keratoplasty. *Am J Ophthalmol.* 2010; 150(3):360-365.e2. doi:10.1016/j.ajo.2010.04.017
2. Ehlers J P, Tam T, Kaiser P K, Martin D F, Smith G M, Srivastava S K. Utility of Intraoperative Optical Coherence Tomography During Vitrectomy Surgery for Vitreomacular Traction Syndrome. *Retina.* 2014; 34(7):1341-1346. doi:10.1097/IAE.0000000000000123
3. Ehlers J P, Ohr M P, Kaiser P K, Srivastava S K. Novel Microarchitectural Dynamics in Rhegmatogenous Detachments Identified with Intraoperative Optical Coherence Tomography. *Retina.* 2013; 33(7):1428-1434. doi:10.1097/IAE.0b013e31828396b7

4. Ehlers J P, Kernstine K, Farsiu S, Sarin N, Maldonado R, Toth C A. Analysis of Pars Plana Vitrectomy for Optic Pit-Related Maculopathy With Intraoperative Optical Coherence Tomography. *Arch Ophthalmol.* 2011; 129 (11):1483. doi:10.1001/archophthalmol.2011.316
5. Carrasco-Zevallos O, Keller B, Viehland C, et al. 4D microscope-integrated OCT improves accuracy of ophthalmic surgical maneuvers. In: Manns F, Söderberg P G, Ho A, eds. *Proceedings of SPIE;* 2016:969306. doi: 10.1117/12.2212857
6. Heiland M, Schulze D, Blake F, Schmelzle R. Intraoperative imaging of zygomaticomaxillary complex fractures using a 3D C-arm system. *Int J Oral Maxillofac Surg.* 2005; 34(4):369-375. doi:10.1016/j.ijom.2004.09.010
7. Senft C, Bink A, Franz K, Vatter H, Gasser T, Seifert V. Intraoperative MRI guidance and extent of resection in glioma surgery: a randomised, controlled trial. *Lancet Oncol.* 2011; 12(11):997-1003. doi:10.1016/51470-2045 (11)70196-6
8. Tormenti M J, Kostov D B, Gardner P A, Kanter A S, Spiro R M, Okonkwo D O. Intraoperative computed tomography image-guided navigation for posterior thoracolumbar spinal instrumentation in spinal deformity surgery. *Neurosurg Focus.* 2010; 28(3):E11. doi:10.3171/2010.1.FOCUS09275
9. Zausinger S, Scheder B, Uhl E, Heigl T, Morhard D, Tonn J-C. Intraoperative Computed Tomography With Integrated Navigation System in Spinal Stabilizations. *Spine (Phila Pa 1976).* 2009; 34(26):2919-2926. doi:10.1097/BRS.0b013e3181b77b19
10. Roth J, Biyani N, Beni-Adani L, Constantini S. Real-time neuronavigation with high-quality 3D ultrasound SonoWand in pediatric neurosurgery. *Pediatr Neurosurg.* 2007; 43(3):185-191. doi:10.1159/000098830
11. Carrasco-Zevallos O M, Viehland C, Keller B, et al. Review of intraoperative optical coherence tomography: technology and applications [Invited]. *Biomed Opt Express.* 2017; 8(3):1607-1637. doi:10.1364/BOE.8.001607
12. Tao Y K, Srivastava S K, Ehlers J P. Microscope-integrated intraoperative OCT with electrically tunable focus and heads-up display for imaging of ophthalmic surgical maneuvers. *Biomed Opt Express.* 2014; 5(6):1877-1885. doi:10.1364/BOE.5.001877
13. Zhang K, Kang J U. Real-time intraoperative 4D full-range FD-OCT based on the dual graphics processing units architecture for microsurgery guidance. *Biomed Opt Express.* 2011; 2(4):764-770. doi:10.1364/BOE.2.000764
14. Shen L, Carrasco-Zevallos O, Keller B, et al. Novel microscope-integrated stereoscopic heads-up display for intrasurgical optical coherence tomography. *Biomed Opt Express.* 2016; 7(5):1711-1726. doi:10.1364/BOE.7.001711
15. Viehland C, Keller B, Carrasco-Zevallos O M, et al. Enhanced volumetric visualization for real time 4D intraoperative ophthalmic swept-source OCT. *Biomed Opt Express.* 2016; 7(5):1815. doi:10.1364/BOE.7.001815
16. Carrasco-Zevallos O M, Keller B, Viehland C, et al. Live volumetric (4D) visualization and guidance of in vivo human ophthalmic surgery with intraoperative optical coherence tomography. *Sci Rep.* 2016; 6(1):31689. doi:10.1038/srep31689
17. Ehlers J P, Dupps W J, Kaiser P K, et al. The Prospective Intraoperative and Perioperative Ophthalmic ImagiNg with Optical CoherEncE TomogRaphy (PIONEER) Study: 2-year results. *Am J Ophthalmol.* 2014; 158(5):999-1007. doi:10.1016/j.ajo.2014.07.034
18. Ahlers C, Simader C, Geitzenauer W, et al. Automatic segmentation in three-dimensional analysis of fibrovascular pigmentepithelial detachment using high-definition optical coherence tomography. *Br J Ophthalmol.* 2008; 92(2):197-203. doi:10.1136/bjo.2007.120956
19. Loduca A L, Zhang C, Zelkha R, Shahidi M. Thickness Mapping of Retinal Layers by Spectral-Domain Optical Coherence Tomography. *Am J Ophthalmol.* 2010; 150(6):849-855. doi:10.1016/j.ajo.2010.06.034
20. Beenakker J-W M, Shamonin D P, Webb A G, Luyten G P M, Stoel B C. Automated Retinal Topographic Maps Measured With Magnetic Resonance Imaging. *Invest Ophthalmol Vis Sci.* 2015; 56(2):1033-1039. doi:10.1167/iovs.14-15161
21. Oh I K, Oh J, Yang K-S, Lee K H, Kim S-W, Huh K. Retinal Topography of Myopic Eyes: A Spectral-Domain Optical Coherence Tomography Study. *Investig Opthalmology Vis Sci.* 2014; 55(7):4313. doi:10.1167/iovs.14-14277
22. Nimsky C, Ganslandt O, Cerny S, Hastreiter P, Greiner G, Fahlbusch R. Quantification of, Visualization of, and Compensation for Brain Shift Using Intraoperative Magnetic Resonance Imaging. *Neurosurgery.* 2000; 47(5):1070-1080. doi:10.1097/00006123-200011000-00008
23. Chandra S, Salgo I S, Sugeng L, et al. Characterization of degenerative mitral valve disease using morphologic analysis of real-time three-dimensional echocardiographic images: objective insight into complexity and planning of mitral valve repair. *Circ Cardiovasc Imaging.* 2011; 4(1):24-32. doi:10.1161/CIRCIMAGING.109.924332
24. Tsang W, Weinert L, Sugeng L, et al. The Value of Three-Dimensional Echocardiography Derived Mitral Valve Parametric Maps and the Role of Experience in the Diagnosis of Pathology. *J Am Soc Echocardiogr.* 2011; 24(8):860-867. doi:10.1016/j.echo.2011.05.015
25. Smith M J, Clark C D. Methods for the visualization of digital elevation models for landform mapping. *Earth Surf Process Landforms.* 2005; 30(7):885-900. doi: 10.1002/esp.1210
26. Carrasco-Zevallos O M, Viehland C, Keller B, McNabb R P, Kuo A N, Izatt J A. Close-loop, constant linear velocity spiral scanning for high-speed optical coherence tomography. Manuscript in preparation. 2018.
27. Pasricha N D, Shieh C, Carrasco-Zevallos O M, et al. Real-Time Microscope-Integrated OCT to Improve Visualization in DSAEK for Advanced Bullous Keratopathy. *Cornea.* 2015; 34(12):1606-1610. doi:10.1097/ICO.0000000000000661
28. Pasricha N D, Bhullar P K, Shieh C, et al. Four-dimensional Microscope-Integrated Optical Coherence Tomography to Visualize Suture Depth in Strabismus Surgery. *J Pediatr Ophthalmol Strabismus.* February 2017. doi:10.3928/01913913-20170201-01
29. Kumar A, Kakkar P, Ravani R D, Markan A. Utility of microscope-integrated optical coherence tomography (MIOCT) in the treatment of myopic macular hole retinal detachment. *BMJ Case Rep.* 2017; 2017:bcr-2016-217671. doi:10.1136/bcr-2016-217671

What is claimed is:
1. An imaging system comprising:
an optical coherence tomography (OCT) apparatus configured to capture OCT data of an eye, wherein the OCT data includes images of a mass of the eye over a period of time; and a controller configured to:
  determine areas within the images of the mass of the eye that have a predetermined intensity,
  determine a location within the mass of the eye among only the areas having the predetermined intensity,
  apply a color gradient on the mass of the eye based on a position relative to the determined location within the mass of the eye; and
  control a display to display the mass with the applied color gradient.

2. The imaging system of claim 1, wherein the OCT images include images of one of the retina of the eye, the anterior segment region of the eye, or the lens region of the eye.

3. The imaging system of claim 1, wherein the OCT apparatus captures the OCT images over a period of time.

4. The imaging system of claim 1, wherein the controller comprises a graphics processing unit (GPU) configured to implement the functions of applying the color gradient and controlling the display in a parallel computational technique.

5. The imaging system of claim 1, wherein the display is one of a heads-up display, a computer display, a display within the oculars of the operating microscope, a conventional computer monitor, and an external 3D television display.

6. A method comprising:
  using an optical coherence tomography (OCT) apparatus to capture OCT data of an eye, wherein the OCT data includes images of a mass of the eye over a period of time;
  determining areas within the images of the mass of the eye that have a predetermined intensity;
  determining a location within the mass of the eye among only the areas having the predetermined intensity;
  applying a color gradient on the mass of the eye based on a position relative to the determined location within the mass of the eye; and
  controlling a display to display the mass with the applied color gradient.

7. The method of claim 6, and wherein the OCT images include images one of the retina of the eye, the anterior segment region of the eye, or the lens region of the eye.

8. The method of claim 6, further comprising using the OCT apparatus to capture the OCT images over a period of time.

9. The method of claim 6, further comprising using a graphics processing unit (GPU) for applying the color gradient and controlling the display in a parallel computational technique.

10. The method of claim 6, wherein the display is one of a heads-up display, a computer display, a display within the oculars of the operating microscope, a conventional computer monitor, and an external 3D television display.

11. An imaging system comprising:
  an optical coherence tomography (OCT) apparatus configured to capture OCT data of an eye, wherein the OCT data includes images of a portion of the eye over a period of time; and
  a controller configured to:
    determine movement of the eye relative to an OCT imaging field-of-view;
    determine areas within the images of the portion of the eye that have a predetermined intensity;
    determine a location within the imaged portion of the eye which tracks with the eye movement, wherein the location is determined as being only from among the areas having the predetermined intensity;
    apply a color gradient to rendered OCT images of the eye based on a position relative to the determined location; and
    control a display to display OCT images with the applied color gradient.

12. The imaging system of claim 11, wherein the OCT data is data of the retina of the eye.

13. The imaging system of claim 11, wherein the OCT data is three-dimensional image data of the eye captured by the OCT apparatus over a period of time.

14. The imaging system of claim 11, wherein the determined location within the imaged portion of the eye has an intensity in the 99th percentile of intensity of the imaged portion.

15. The imaging system of claim 11, wherein the determined location within the imaged portion of the eye are voxels of the images of the portion of the eye.

16. The imaging system of claim 11, wherein the determined location is a center or an approximate center within the imaged portion of the eye among areas having the predetermined intensity.

17. The imaging system of claim 11, wherein the controller is configured to implement the functions of determining the location, applying the color gradient, and controlling the display for each image of the portion of the eye acquired over the period of time.

18. The imaging system of claim 11, wherein the controller comprises a graphics processing unit (GPU) configured to implement the functions of determining the location, applying the color gradient, and controlling the display in a parallel computational technique.

19. The imaging system of claim 11, wherein the display is one of a heads-up display and a computer display.

20. The imaging system of claim 11, wherein the controller is configured to:
  receive user input regarding color content and relative depth positions; and
  map user input to three-dimensional (3D) coordinates based on the determined location.

21. The imaging system of claim 20, wherein color mapping is applied along a dimension within a volume of the 3D coordinates.

22. A method comprising:
  using an optical coherence tomography (OCT) apparatus to capture OCT data of an eye, wherein the OCT data includes images of a a portion of the eye over a period of time;
  determining movement of the eye relative to an OCT imaging field-of-view;
  determining areas within the images of the portion of the eye that have a predetermined intensity;
  determining a location within the imaged portion of the eye which tracks with the eye movement, wherein the location is determined as being only from among the areas having the predetermined intensity;
  applying a color gradient to rendered OCT images of the eye based on a position relative to the determined location; and
  displaying the OCT images with the applied color gradient.

23. The method of claim 22, wherein the OCT data is data of the retina of the eye.

24. The method of claim 22, wherein the OCT data is three-dimensional image data of the eye captured by the OCT apparatus over a period of time.

25. The method of claim 22, wherein the determined location within the imaged portion of the eye has an intensity in the 99th percentile of intensity of the imaged portion.

26. The method of claim 22, wherein the determined location within the imaged portion of the eye are voxels of the images of the portion of the eye.

27. The method of claim 22, wherein the determined location is a center or an approximate center of the mass of the eye among areas having the predetermined intensity.

28. The method of claim 22, wherein determining areas, determining the predetermined location, applying the color gradient, and controlling the display are implemented for each image of the mass of the eye acquired over the period of time.

29. The method of claim 22, further comprising using a graphics processing unit (GPU) configured to implement determining areas, determining the predetermined location, applying the color gradient, and controlling the display in a parallel computational technique.

30. The method of claim 22, wherein the display is one of a heads-up display a computer display, a display within the oculars of the operating microscope, a conventional computer monitor, and an external 3D television display.

31. The method of claim 22, further comprising:
   receive user input regarding color content and relative depth positions; and
   map user input to three-dimensional (3D) coordinates based on the determined location.

32. The method of claim 31, wherein color mapping is applied along a dimension within a volume of the 3D coordinates.

* * * * *